(12) United States Patent
Bosch et al.

(10) Patent No.: US 7,842,232 B2
(45) Date of Patent: Nov. 30, 2010

(54) STERILIZATION OF DISPERSIONS OF NANOPARTICULATE ACTIVE AGENTS WITH GAMMA RADIATION

(75) Inventors: H. William Bosch, Bryn Mawr, PA (US); Janine Keller, King of Prussia, PA (US)

(73) Assignee: Elan Pharma International, Ltd., Athlone, County Westmeath (IE)

( * ) Notice: Subject to any disclaimer, the term of this patent is extended or adjusted under 35 U.S.C. 154(b) by 969 days.

(21) Appl. No.: 10/851,661

(22) Filed: May 24, 2004

(65) Prior Publication Data

US 2010/0255102 A1    Oct. 7, 2010

Related U.S. Application Data

(60) Provisional application No. 60/472,434, filed on May 22, 2003.

(51) Int. Cl.
- A61K 49/00 (2006.01)
- A61K 9/00 (2006.01)
- A61K 9/14 (2006.01)
- A61K 33/00 (2006.01)
- A61F 13/00 (2006.01)
- A01N 59/24 (2006.01)
- A61L 2/00 (2006.01)

(52) U.S. Cl. .................... 422/22; 424/9.1; 424/400; 424/422; 424/484; 424/489; 424/600

(58) Field of Classification Search .................. 422/22; 977/915; 424/9.1, 400, 422, 484, 489, 600
See application file for complete search history.

(56) References Cited

U.S. PATENT DOCUMENTS

| | | |
|---|---|---|
| 4,178,695 A | 12/1979 | Erbeia |
| 4,330,626 A | 5/1982 | Blair et al. |
| 4,783,484 A | 11/1988 | Violante et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,362,442 A | 11/1994 | Kent |
| 5,384,124 A | 1/1995 | Courteille et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,716,981 A | 2/1998 | Hunter et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,858,410 A | 1/1999 | Muller et al. |

(Continued)

FOREIGN PATENT DOCUMENTS

EP    0 601 619 A2    6/1994

(Continued)

OTHER PUBLICATIONS

Seino et al., Hyrdogen Evolution From Water Dispersing Nanoparticles Irradiated With Gamma-Ray/Size Effect and Dose Rate Effect, 2001, Scripta Materialia, 44, pp. 1709-1712.*

(Continued)

*Primary Examiner*—Walter D Griffin
*Assistant Examiner*—Lydia Edwards
(74) *Attorney, Agent, or Firm*—Foley & Lardner LLP

(57) ABSTRACT

The present invention relates to methods for sterilization of dispersions of one or more nanoparticulate active agents via gamma irradiation.

43 Claims, No Drawings

U.S. PATENT DOCUMENTS

| | | | |
|---|---|---|---|
| 5,862,999 A | 1/1999 | Czekai et al. | |
| 5,914,122 A | 6/1999 | Otterbeck et al. | |
| 5,922,355 A | 7/1999 | Parikh et al. | |
| 5,993,781 A | 11/1999 | Snell et al. | |
| 6,039,932 A | 3/2000 | Govind et al. | |
| 6,045,829 A | 4/2000 | Liversidge et al. | |
| 6,066,292 A | 5/2000 | Purwar | |
| 6,068,858 A | 5/2000 | Liversidge et al. | |
| 6,123,923 A * | 9/2000 | Unger et al. | 424/9.52 |
| 6,139,870 A | 10/2000 | Verrecchia | |
| 6,153,225 A | 11/2000 | Lee et al. | |
| 6,165,506 A | 12/2000 | Jain et al. | |
| 6,221,400 B1 | 4/2001 | Liversidge et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,316,029 B1 | 11/2001 | Jain et al. | |
| 6,375,986 B1 * | 4/2002 | Ryde et al. | 424/489 |
| 6,392,036 B1 | 5/2002 | Karlsson et al. | |
| 6,428,814 B1 * | 8/2002 | Bosch et al. | 424/501 |
| 6,431,478 B1 | 8/2002 | Reed et al. | |
| 6,432,381 B2 | 8/2002 | Liversidge et al. | |
| 6,451,339 B2 | 9/2002 | Patel et al. | |
| 6,464,958 B1 * | 10/2002 | Bernini et al. | 424/43 |
| 6,468,994 B1 | 10/2002 | Bisrat et al. | |
| 6,512,023 B1 * | 1/2003 | Malofsky et al. | 523/111 |
| 6,551,612 B2 * | 4/2003 | Benowitz | 424/450 |
| 6,811,767 B1 | 11/2004 | Bosch et al. | |
| 7,064,187 B2 | 6/2006 | Stone | |
| 2001/0049354 A1 | 12/2001 | Shalaev et al. | |
| 2002/0012675 A1 | 1/2002 | Jain et al. | |
| 2002/0037877 A1 | 3/2002 | Singh et al. | |
| 2002/0042378 A1 | 4/2002 | Reich et al. | |
| 2003/0077329 A1 * | 4/2003 | Kipp et al. | 424/489 |
| 2003/0078617 A1 | 4/2003 | Schwartz et al. | |
| 2003/0095928 A1 | 5/2003 | McGurk et al. | |
| 2003/0143106 A1 | 7/2003 | Kent et al. | |
| 2003/0185869 A1 * | 10/2003 | Wertz et al. | 424/405 |
| 2003/0219461 A1 * | 11/2003 | Britten et al. | 424/204.1 |
| 2004/0106679 A1 * | 6/2004 | Klaveness et al. | 514/561 |

FOREIGN PATENT DOCUMENTS

| | | |
|---|---|---|
| EP | 0 605 024 A2 | 7/1994 |
| EP | 0 636 365 A1 | 2/1995 |
| EP | 1 310 243 A1 | 5/2003 |
| EP | 1 454 636 A1 | 9/2004 |
| GB | 2 222 081 | 2/1990 |
| JP | 5-15574 | 1/1993 |
| WO | WO 98/48847 A1 | 11/1998 |
| WO | WO 00/09096 A1 | 2/2000 |
| WO | WO 00/25746 | 5/2000 |
| WO | WO 00/53164 A1 | 9/2000 |
| WO | WO 02/10120 A1 | 2/2002 |
| WO | WO 01/78689 A2 | 10/2002 |
| WO | WO 02/098565 A1 | 12/2002 |
| WO | WO 03/035031 A1 | 5/2003 |
| WO | WO 2004/032980 A1 | 4/2004 |

OTHER PUBLICATIONS

Sintzel et al. Influence of irradiation sterilization on a semi-solid poly(ortho ester), 1998, International Journal of Pharmaceutics, 175, pp. 165-176.*

Faisant et al., The effect of gamma-irradiation on drug release from biorodible microparticles: a quantitatve treatment, 2002, International Journal of Pharmaceutics, 242, pp. 281-284.*

Lindahl et al., "Characterization of Fluids from the Stomach and Proximal Jejunum in Men and Women", *Pharmaceutical Research*, vol. 14, No. 4, pp. 497-502 (1997).

Reid, "Gamma Processing Technology: An Alternative Technology for Terminal Sterilization of Parenterals", *PDA Journal of Pharmaceutical Science and Technology*, Bethesda, MD, US, vol. 49, No. 2, 1995, pp. 83-89, XP002087677, ISSN: 1079-7440.

U.S. Appl. No. 60/353,230, filed Feb. 4, 2002, Wertz, et al.

U.S. Appl. No. 60/429,078, filed Nov. 26, 2002, Stone.

International Preliminary Report on Patentability for related International Patent Application No. PCT/US2004/014528, issued Nov. 25, 2005, 9 pgs.

Written Opinion of the International Searching Authority for related International Patent Application No. PCT/US2004/014528, issued Nov. 25, 2005, 8 pgs.

Notice of Reasons for Rejection cited in related Japanese Patent Application No. 2006-532906, dated Nov. 26, 2008, 5 pgs.

Rudnic et al., "Oral Solid Dosage Forms", *Remington's Pharmaceutical Sciences*, Chapter 89, pp. 1633-1658 (Mack Publishing Company, 1990).

Shalaev et al., "Protection of a protein against irradiation-induced degradation by additives in the solid state," *Radiation Physics & Chemistry*, vol. 66, pp. 237-245 (2003).

Office Action dated Jan. 11, 2007 from related U.S. Appl. No. 10/654,600, 30 pgs.

Office Action dated Jun. 20, 2007 from related U.S. Appl. No. 10/654,600, 21 pgs.

Office Action dated Feb. 5, 2008 from related U.S. Appl. No. 10/654,600, 22 pgs.

Office Action dated Jun. 12, 2008 from related U.S. Appl. No. 10/654,600, 18 pgs.

Office Action dated Dec. 4, 2008 from related U.S. Appl. No. 10/654,600, 18 pgs.

Office Action dated May 22, 2009 from related U.S. Appl. No. 10/654,600, 19 pgs.

Office Action dated May 25, 2010 from related U.S. Appl. No. 10/654,600, 21 pgs.

Office Action dated Feb. 17, 2010 from related U.S. Appl. No. 10/654,600, 22 pgs.

Song et al., "Formulation and characterization of biodegradable nanoparticles for intravascular local drug delivery," *Journal of Controlled Release* (1997), vol. 43, pp. 197-212, XP0044256642.

Mohr et al., "Gamma irradiation for terminal sterilization of 17,β-estradiol loaded poly-(D,L-lactide-co-glycolide) microparticles," *Journal of Controlled Release* (1999), vol. 61, pp. 203-217, XP004362977.

* cited by examiner

STERILIZATION OF DISPERSIONS OF NANOPARTICULATE ACTIVE AGENTS WITH GAMMA RADIATION

FIELD OF THE INVENTION

The present invention relates to methods for sterilization of dispersions of one or more nanoparticulate active agents via gamma irradiation, and compositions comprising such sterilized dispersions. The one or more nanoparticulate active agents have an effective average particle size of less than about 2 microns. The sterilized dispersions exhibit excellent chemical and physical stability, homogeneity, and uniformity.

BACKGROUND OF THE INVENTION

A. Background Regarding Gamma Irradiation

Irradiating a product with gamma radiation is one method of sterilizing a pharmaceutical product. Gamma irradiation is effective in destroying viruses and bacteria when given in high total doses. Unlike other sterilization methods, such as ethylene oxide sterilization, radiation sterilization has the advantages of high penetrating ability and instantaneous effects, without the need to control temperature, pressure, vacuum, or humidity.

U.S. Pat. No. 4,330,626 describes a process of preparing urease from jack beans. As part of the process, the beans are irradiated to reduce microbial contamination. The irradiation of the beans occurs prior to any size reduction of the seeds of the jack beans. This is done because there is loss of activity of the urease by irradiating the beans after particle size reduction.

U.S. Pat. No. 6,066,292 describes the sterilization of pharmaceuticals including a suspension by a technique other than gamma radiation. Gamma irradiation is generally discussed in the background of the invention.

B. Background Regarding Nanoparticulate Active Agent Compositions

Nanoparticulate compositions, first described in U.S. Pat. No. 5,145,684 ("the '684 patent"), are particles consisting of a poorly soluble active agent having associated with or adsorbed on the surface thereof a surface stabilizer. The '684 patent also describes methods of making such nanoparticulate compositions. Nanoparticulate compositions are desirable because with a decrease in particle size, and a consequent increase in surface area, a composition is rapidly dissolved and absorbed following administration. The '684 patent does not teach or suggest sterilization of nanoparticulate compositions via gamma irradiation.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. Nos. 5,298,262 for "Use of Ionic Cloud Point Modifiers to Prevent Particle Aggregation During Sterilization;" 5,302,401 for "Method to Reduce Particle Size Growth During Lyophilization;" 5,318,767 for "X-Ray Contrast Compositions Useful in Medical Imaging;" 5,326,552 for "Novel Formulation For Nanoparticulate X-Ray Blood Pool Contrast Agents Using High Molecular Weight Non-ionic Surfactants;" 5,328,404 for "Method of X-Ray Imaging Using Iodinated Aromatic Propanedioates;" 5,336,507 for "Use of Charged Phospholipids to Reduce Nanoparticle Aggregation;" 5,340,564 for "Formulations Comprising Olin 10-G to Prevent Particle Aggregation and Increase Stability;" 5,346,702 for "Use of Non-Ionic Cloud Point Modifiers to Minimize Nanoparticulate Aggregation During Sterilization;" 5,349,957 for "Preparation and Magnetic Properties of Very Small Magnetic-Dextran Particles;" 5,352,459 for "Use of Purified Surface Modifiers to Prevent Particle Aggregation During Sterilization;" 5,399,363 and 5,494,683, both for "Surface Modified Anticancer Nanoparticles;" 5,401,492 for "Water Insoluble Non-Magnetic Manganese Particles as Magnetic Resonance Enhancement Agents;" 5,429,824 for "Use of Tyloxapol as a Nanoparticulate Stabilizer;" 5,447,710 for "Method for Making Nanoparticulate X-Ray Blood Pool Contrast Agents Using High Molecular Weight Non-ionic Surfactants;" 5,451,393 for "X-Ray Contrast Compositions Useful in Medical Imaging;" 5,466,440 for "Formulations of Oral Gastrointestinal Diagnostic X-Ray Contrast Agents in Combination with Pharmaceutically Acceptable Clays;" 5,470,583 for "Method of Preparing Nanoparticle Compositions Containing Charged Phospholipids to Reduce Aggregation;" 5,472,683 for "Nanoparticulate Diagnostic Mixed Carbamic Anhydrides as X-Ray Contrast Agents for Blood Pool and Lymphatic System Imaging;" 5,500,204 for "Nanoparticulate Diagnostic Dimers as X-Ray Contrast Agents for Blood Pool and Lymphatic System Imaging;" 5,518,738 for "Nanoparticulate NSAID Formulations;" 5,521,218 for "Nanoparticulate Iododipamide Derivatives for Use as X-Ray Contrast Agents;" 5,525,328 for "Nanoparticulate Diagnostic Diatrizoxy Ester X-Ray Contrast Agents for Blood Pool and Lymphatic System Imaging;" 5,543,133 for "Process of Preparing X-Ray Contrast Compositions Containing Nanoparticles;" 5,552,160 for "Surface Modified NSAID Nanoparticles;" 5,560,931 for "Formulations of Compounds as Nanoparticulate Dispersions in Digestible Oils or Fatty Acids;" 5,565,188 for "Polyalkylene Block Copolymers as Surface Modifiers for Nanoparticles;" 5,569,448 for "Sulfated Non-ionic Block Copolymer Surfactant as Stabilizer Coatings for Nanoparticle Compositions;" 5,571,536 for "Formulations of Compounds as Nanoparticulate Dispersions in Digestible Oils or Fatty Acids;" 5,573,749 for "Nanoparticulate Diagnostic Mixed Carboxylic Anydrides as X-Ray Contrast Agents for Blood Pool and Lymphatic System Imaging;" 5,573,750 for "Diagnostic Imaging X-Ray Contrast Agents;" 5,573,783 for "Redispersible Nanoparticulate Film Matrices With Protective Overcoats;" 5,580,579 for "Site-specific Adhesion Within the GI Tract Using Nanoparticles Stabilized by High Molecular Weight, Linear Poly(ethylene Oxide) Polymers;" 5,585,108 for "Formulations of Oral Gastrointestinal Therapeutic Agents in Combination with Pharmaceutically Acceptable Clays;" 5,587,143 for "Butylene Oxide-Ethylene Oxide Block Copolymers Surfactants as Stabilizer Coatings for Nanoparticulate Compositions;" 5,591,456 for "Milled Naproxen with Hydroxypropyl Cellulose as Dispersion Stabilizer;" 5,593,657 for "Novel Barium Salt Formulations Stabilized by Non-ionic and Anionic Stabilizers;" 5,622,938 for "Sugar Based Surfactant for Nanocrystals;" 5,628,981 for "Improved Formulations of Oral Gastrointestinal Diagnostic X-Ray Contrast Agents and Oral Gastrointestinal Therapeutic Agents;" 5,643,552 for "Nanoparticulate Diagnostic Mixed Carbonic Anhydrides as X-Ray Contrast Agents for Blood Pool and Lymphatic System Imaging;" 5,718,388 for "Continuous Method of Grinding Pharmaceutical Substances;" 5,718,919 for "Nanoparticles Containing the R(−)Enantiomer of Ibuprofen;" 5,747,001 for "Aerosols Containing Beclomethasone Nanoparticle Dispersions;" 5,834,025 for "Reduction of Intravenously Administered Nanoparticulate Formulation Induced Adverse Physiological Reactions;" 6,045,829 "Nanocrystalline Formulations of Human Immunodeficiency Virus (HIV) Protease Inhibitors Using Cellulosic Surface Stabilizers;" 6,068,858 for "Methods of Making Nanocrystalline Formulations of Human Immunodeficiency Virus (HIV) Protease Inhibitors Using Cellulosic Surface Stabilizers;" 6,153,225 for "Injectable Formulations of Nanoparticulate Naproxen;" 6,165,506 for "New Solid Dose Form of Nanoparticulate Naproxen;" 6,221,400 for "Methods of Treating Mammals Using Nanocrystalline Formulations of Human Immunodeficiency Virus (HIV) Protease Inhibitors;" 6,264,922 for "Nebulized Aerosols Containing Nanoparticle Dispersions;" 6,267,989 for "Methods for Preventing Crystal Growth and Particle Aggregation in Nanoparticle Compositions;" 6,270,806 for "Use of PEG-Derivatized Lipids as Surface Stabilizers for Nanoparticulate Compositions;" 6,316,029 for "Rapidly Disintegrating Solid Oral Dosage Form," 6,375,986 for "Solid Dose Nanoparticulate Compositions Comprising a Synergistic Combination of a Polymeric Surface Stabilizer and Dioctyl Sodium Sulfosuccinate;" 6,428,814 for "Bioadhesive Nanoparticulate Compositions Having Cationic Surface Stabilizers;" 6,431,478 for "Small Scale Mill," and 6,432,381 for "Methods for Targeting Drug Delivery to the Upper and/or Lower Gastrointestinal Tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. Nos. 4,783,484 for "Particulate Composition and Use Thereof as Antimicrobial Agent;" 4,826,689 for "Method for Making Uniformly Sized Particles from Water-Insoluble Organic Compounds;" 4,997,454 for "Method for Making'Uniformly-Sized Particles From Insoluble Compounds;" 5,741,522 for "Ultrasmall, Non-aggregated Porous Particles of Uniform Size for Entrapping Gas Bubbles Within and Methods;" and 5,776,496, for "Ultrasmall Porous Particles for Enhancing Ultrasound Back Scatter." None of these references teaches gamma irradiation of nanoparticulate active agent compositions.

C. Background Relating to Sterilization of Nanoparticulate Active Agent Compositions There are three commonly used methods for sterilizing pharmaceutical products: heat sterilization, sterile filtration, and ethylene oxide exposure.

1. Heat Sterilization of Nanoparticulate Active Agent Compositions

One of the problems that may be encountered with heat sterilization of nanoparticulate active agent compositions is the solubilization and subsequent recrystallization of the component active agent particles. This process results in an increase in the size distribution of the active agent particles. In cases where the nanoparticulate active agent formulations contain surface modifiers, which have cloud points lower than the sterilization temperature (generally about 121° C.), the surface modifiers may desorb or disassociate from the nanoparticulate active agent surfaces and precipitate from solution at or below the sterilization temperature. Thus, some nanoparticulate active agent formulations also exhibit particle aggregation following exposure to elevated temperatures during the heat sterilization process.

Crystal growth and particle aggregation in nanoparticulate active agent preparations are highly undesirable for several reasons. The presence of large crystals in the nanoparticulate active agent composition may cause undesirable side effects, especially when the preparation is in an injectable formulation. This is also true for particle aggregation, as injectable formulations preferably have an effective average particle size of no greater than 250 nm. Larger particles formed by particle aggregation and recrystallization can interfere with blood flow, causing pulmonary embolism and death.

In addition, with both injectable and oral formulations the presence of large crystals, and therefore varying particle sizes, and/or particle aggregation can change the pharmacokinetic profile of the administered active agent. For oral formulations, the presence of large crystals or aggregates creates a variable bioavailability profile because smaller particles dissolve faster than the larger aggregates or larger crystal particles. A faster rate of dissolution is associated with greater bioavailability and a slower rate of dissolution is associated with a lower bioavailability. This is because bioavailability is proportional to the surface area of an administered drug and, therefore, bioavailability increases with a reduction in the particle size of the dispersed agent (see U.S. Pat. No. 5,662,883).

With a composition having widely varying particle sizes, bioavailability becomes highly variable and inconsistent and dosage determinations become difficult. Moreover, because such crystal growth and particle aggregation are uncontrollable and unpredictable, the quality of the nanoparticulate compositions is inconsistent. For intravenously injected particulate formulations, the presence of large crystals or aggregates can induce an immune system response which causes the larger particles to be transported by macrophage cells to the liver or spleen and metabolized, in addition to the embolytic effects described above.

Aggregation of nanoparticle active agent compositions upon heating is directly related to the precipitation of the surface stabilizer at temperatures above the cloud point of the surface stabilizer. At this point, the bound surface stabilizer molecules are likely to dissociate from the nanoparticles and precipitate, leaving the nanoparticles unprotected. The unprotected nanoparticles then aggregate into clusters of particles.

Several methods have been suggested in the prior art for preventing such crystal growth and particle aggregation following heat sterilization, including adding a cloud point modifier or crystal growth modifier to the nanoparticulate active agent composition and purifying the surface stabilizer. For example, U.S. Pat. No. 5,298,262 describes the use of an anionic or cationic cloud point modifier in nanoparticulate active agent compositions and U.S. Pat. No. 5,346,702 describes nanoparticulate active agent compositions having a nonionic surface stabilizer and a non-ionic cloud point modifier. The cloud point modifier enables heat sterilization of the nanoparticulate active agent compositions with low resultant particle aggregation. U.S. Pat. No. 5,470,583 describes nanoparticulate active agent compositions having a non-ionic surface stabilizer and a charged phospholipid as a cloud point modifier.

The prior art also describes methods of limiting crystal growth in a nanoparticulate active agent composition by adding a crystal growth modifier (see U.S. Pat. Nos. 5,662,883 and 5,665,331). In addition, U.S. Pat. No. 5,302,401 describes nanoparticulate active agent compositions having polyvinylpyrrolidone (PVP) as a surface stabilizer and sucrose as a cryoprotectant (allowing the nanoparticles to be lyophilized). The compositions exhibit minimal particle aggregation following lyophilization.

All of these various prior art methods share one common feature: they require an additional substance added to the nanoparticulate active agent formulation to inhibit or prevent crystal growth and particle aggregation of the nanoparticulate active agent composition. The addition of such a substance can be detrimental as it may induce adverse effects, particularly for injectable formulations. Thus, this minimizes the usefulness of such substances in pharmaceutical compositions. In addition, the requirement of an additional substance to obtain a stable composition increases production costs.

Another method of limiting particle aggregation or crystal growth of nanoparticulate active agent compositions during sterilization known prior to the present invention was the use of purified surface stabilizers. U.S. Pat. No. 5,352,459 describes nanoparticulate active agent compositions having a purified surface stabilizer (having less than 15% impurities) and a cloud point modifier. Purification of surface stabilizers can be expensive and time consuming, thus significantly raising production costs of compositions requiring such stabilizers to produce a stable nanoparticulate active agent composition.

2. Sterile Filtration

Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize conventional suspensions of micron-sized drug particles because the drug substance particles are too large to pass through the membrane pores. In principle, 0.2 µm filtration can be used to sterilize nanoparticulate active agent compositions. However, because nanoparticulate active agent compositions have a size range, many of the particles of a typical nanoparticulate active agent composition having an average particle size of 200 nm may have a size greater than 200 nm. Such larger particles tend to clog the sterile filter. Thus, only nanoparticulate active agent compositions having very small average particle sizes can be sterile filtered.

3. Ethylene Oxide Method

The ethylene oxide method has been a widely used sterilization method for suspension/dispersion products where product or components are thermolabile. Most of the currently marketed products utilize this technique by which individual components are sterilized using this method and then processed or assembled together aseptically. The technique, however, requires the elimination of residual ethylene oxide from the product, which is a time consuming and difficult process with the possibility of residual ethylene oxide contaminating the final drug product.

There remains a need in the art for additional methods of sterilizing nanoparticulate active agent compositions. The present invention satisfies this need.

SUMMARY OF THE INVENTION

The present invention is directed to the surprising discovery that dispersions of one or more nanoparticulate active agents can be successfully sterilized, including terminal sterilization, via gamma irradiation. Following sterilization, the nanoparticulate particle size of the active agent present in the dispersion is substantially similar to the original nanoparticulate active agent particle size.

One aspect of the invention is directed to methods of sterilizing dispersions of one or more nanoparticulate active agents via gamma irradiation. Such a method comprises exposing a dispersion of one or more nanoparticulate active agents to a suitable dosage of gamma irradiation. The length of time of irradiation or the total dose of irradiation delivered will depend on the bioburden of the product, the nature of the contaminant, and the nature of the product. The method does not substantially degrade or substantially chemically alter the nanoparticulate active agent or substantially alter the nanoparticulate active agent particle size. Moreover, the method produces a safe and sterile product in compliance with cGMP requirements.

The method according to the invention can be carried out at ambient temperature and does not require the heating, freezing, filtration, or chemical treatment of the product before the process is carried out. This offers another significant advantage of the present process as it avoids some of the extra treatment steps of the prior art processes.

Another aspect of the invention is directed to dispersions of one or more nanoparticulate active agent compositions sterilized via gamma irradiation, or dry dosage forms prepared from such dispersions. Such compositions comprise at least one poorly soluble active agent and one or more surface stabilizers associated with or adsorbed to the surface of the active agent. The active agent has an effective average particle size of less than about 2 microns.

The present invention is further directed to pharmaceutical compositions comprising a sterilized dispersion of one or more nanoparticulate active agents, or a dry dosage form of such a sterilized dispersion. The pharmaceutical compositions preferably comprise a pharmaceutically acceptable carrier as well as any desired excipients.

Yet another aspect of the invention encompasses a method of treating a mammal in need comprising administering a therapeutically effective amount of a sterilized dispersion of one or more nanoparticulate active agents, or a dry dosage form prepared from such a dispersion.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to the surprising and unexpected discovery of a new method for the sterilization, including terminal sterilization, of dispersions of one or more nanoparticulate active agents. Dispersions of one or more nanoparticulate active agents, prepared according to methods known in the art, are irradiated with gamma radiation for a period of time sufficient to sterilize the active agent nanoparticles.

The gamma irradiated dispersion of one or more nanoparticulate active agents can then be formulated into any suitable dosage form, such as solid, semi-solid, or liquid dosage form, including dosage forms for oral, pulmonary, nasal, parenteral, rectal, local, buccal, or topical administration. The invention is particularly useful for aqueous dosage forms which can be conducive to contamination, such as injectable, aerosol, or ocular dosage forms, or liquid dosage forms for administration to the ear. The sterilized dispersion can be formulated into a dry powder, such as a lyophilized powder, spray dried powder, or spray granulated powder of a nanoparticulate active agent dispersion. The dosage form can also be a controlled release formulation, solid dose fast melt formulation, aerosol formulation, lyophilized formulation, tablet, solid lozenge, capsule, powder, ocular formulation, a formulation for administration to the ear, or a liquid for injection.

The dispersion of nanoparticulate active agent particles can be subjected to gamma radiation, preferably at ambient temperature. This temperature remains relatively constant during the period of irradiation. The gamma radiation is applied in an amount sufficient to destroy substantially all of the microbial contamination in the dispersion. In addition, the rate of radiation generated in the radiation chamber is relatively constant during the entire radiation period. The total amount of gamma radiation that dispersion is exposed to has been experimentally verified to: (1) show only a modest increase in particle size on storage following exposure to gamma irradiation, (2) maintain the integrity of the nanoparticulate active agent, and (3) to show generally acceptable impurity concentrations following gamma irradiation. The application of the gamma radiation does not significantly degrade the active agent or reduce the active agent's efficacy. The present invention enables products which meet cGMP requirements for sterile products without harming the active agent.

In a preferred aspect of the invention, the gamma radiation is applied in a cumulative amount of 25 kGray. Generally, the gamma radiation will normally be applied in a range of about 5 kGray to about 50 kGray, about 5 kGray to about 25 kGray, about 5 kGray to about 20 kGray, about 5 to about 15 kGray, or about 5 to about 10 kGray. Multiple doses of radiation can be utilized to achieve a desired cumulative radiation dosage.

The microbial contamination which is to be destroyed is generally that of bacterial contamination and mycoplasma contamination.

Surprisingly, following sterilization the dispersion of one or more nanoparticulate active agents exhibits unexpected overall stability, maintaining the pre-sterilized physical and chemical properties, while meeting cGMP requirements for sterility. The overall stability of the gamma irradiated dispersions of nanoparticulate active agents was measured in terms of active agent particle size and content of degradation products. The results are contrary to what would be expected, given disclosures in the prior art. For example, B. Reid, "Gamma Processing Technology An Alternative Technology for Terminal Sterilization of Parenterals," *PDA J. of Pharm. Sci. & Tech.*, 49:83-89 (1995), describes the use of gamma radiation for sterilization of parenterals. At page 87, col. 2, ¶ 6, the reference teaches that "since water is the major source of free radicals, many finished products containing water are difficult, if not impossible, to treat without unacceptably damaging the product."

It is particularly unexpected that gamma irradiation of the dispersion of one or more nanoparticulate active agents does not significantly alter the particle size of the one or more active agents. This is significant because if the sterilized product formed aggregates or large crystals, the dispersion would lose the benefits afforded by being formulated into a nanoparticulate active agent composition.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Conventional active agents or drugs" refers to non-nanoparticulate compositions of active agents or solubilized active agents or drugs. Non-nanoparticulate active agents have an effective average particle size of greater than about 2 microns.

The term "microbial" with respect to contamination, as used herein is deemed to include all biological contaminants including bacteria, yeast, and molds.

As used herein with reference to stable drug particles, "stable" means that the drug particles are substantially chemically stable, as measured by degradent concentrations, and do not appreciably flocculate or agglomerate due to interparticle attractive forces or otherwise increase in particle size.

The term "sterilize" as used in the present application generally means to inactivate substantially all biological contaminants present in the product. In normal pharmaceutical applications, the term "sterilize" is defined as a 6-log (1 million-fold) reduction in the bioburden.

"Therapeutically effective amount" as used herein with respect to an active agent dosage, shall mean that dosage that provides the specific pharmacological response for which the active agent is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that active agent dosages are, in particular instances, measured as oral dosages, or with reference to drug levels as measured in blood.

A. Combination Compositions

The dispersions to be sterilized can comprise multiple active agents, compositions of one or more active agents having multiple particle sizes, or a combination thereof. For example, a dispersion can comprise: (1) nanoparticulate active agent A and nanoparticulate active agent B; (2) nanoparticulate active agent A and microparticulate active agent A; (3) nanoparticulate active agent A and microparticulate active agent B; (3) nanoparticulate active agent A having an effective average particle size of 250 nm and nanoparticulate active agent A having an effective average particle size of 800 nm, or combinations thereof.

1. Compositions Comprising Microparticulate Active Agents

Sterilized microparticulate active agent particles can be combined with the dispersion of one or more nanoparticulate active agent particles, either prior or subsequent to gamma irradiation, to provide for a sustained or controlled release composition. Such sterilized microparticulate active agent particles can also be combined with a sterilized dispersion which has been processed into a powder or other dry dosage form.

The combination of very small active agent particles, i.e., nanoparticulate active agent particles, in combination with larger active agent particles, i.e., micronized active agent particles, can enable obtaining the simultaneous presentation of immediate-release (IR) and controlled-release (CR) active agent components. The micronized active agent particles and nanoparticulate active agent particles can be the same active agent or different active agents.

For the purposes of this invention, "nanoparticulate" active agents have an effective average particle size of less than about 2 microns and micronized active agents have an effective average particle size of greater than about 2 microns. The micronized active agent particles can be sterilized via gamma irradiation simultaneously with the nanoparticulate active agent particles or in a separate process using gamma irradiation or another suitable sterilization method.

The nanoparticulate active agent particles, representing the IR component, afford rapid in vivo dissolution, owing to their small size and attendant large specific surface. The micronized active agent particles, representing the CR component, afford slower in vivo dissolution, owing to a comparatively large particle size and small attendant specific surface.

IR and CR components representing a wide range of in vivo dissolution rates (and hence, in vivo input rates for absorption) can be engineered through precise control of active agent particle size. Thus, the compositions can comprise a mixture of nanoparticulate active agent particles, wherein each population of particles has a defined size correlating with a precise release rate, and the compositions can comprise a mixture of microparticulate active agent particles, wherein each population of particles has a defined size correlating with a precise release rate.

2. Compositions Comprising Multiple Nanoparticulate Particle Sizes

In yet another embodiment of the invention, a dispersion of a first nanoparticulate active agent providing a desired pharmacokinetic profile combined with at least one other dispersion of a nanoparticulate active agent that generates a desired different pharmacokinetic profile. More than two dispersions of nanoparticulate active agents can be combined. While the first active agent dispersion has a nanoparticulate particle size, the additional one or more active agents can be nanoparticulate, solubilized, or have a conventional microparticulate particle size.

The second, third, fourth, etc., active agent dispersions can differ from the first, and from each other, for example: (1) in the effective average particle sizes of the active agent; or (2) in the dosage of the active agent.

Preferably where co-administration of a "fast-acting" formulation and a "longer-lasting" formulation is desired, the two formulations are combined within a single composition, for example a dual-release composition.

B. Active Agents

The active agent may be present either substantially in the form of one optically pure enantiomer or as a mixture, racemic or otherwise, of enantiomers. In addition, the active agent exists as a discrete, crystalline phase, as an amorphous phase, a semi-crystalline phase, a semi-amorphous phase, or a combination thereof.

Exemplary active agents can be therapeutic or diagnostic agents, collectively referred to as "drugs". A therapeutic agent can be a pharmaceutical agent, including biologics such as proteins, peptides, and nucleotides, or a diagnostic agent, such as a contrast agent, including x-ray contrast agents.

Preferably the active agent is poorly soluble in at least one liquid dispersion media. By "poorly soluble" it is meant that the active agent has a solubility in a liquid dispersion media of less than about 30 mg/mL, preferably less than about 10 mg/mL, and more preferably less than about 1 mg/mL. Such a liquid dispersion media can be, for example, water, aqueous salt solutions, oils such as safflower oil, and solvents such as ethanol, t-butanol, hexane, and glycol.

The active agent can be selected from a variety of known classes of drugs, including, for example, COX-2 inhibitors, retinoids, anticancer agents, NSAIDS, proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (e.g., hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

The active agents are commercially available and/or can be prepared by techniques known in the art.

C. Surface Stabilizers for Nanoparticulate Active Agents

If the active agent has a nanoparticulate particle size, with "nanoparticulate" being defined as an effective average particle size of less than about 2 microns, then the active agent generally will have at least one surface stabilizer associated with or adsorbed to the surface of the active agent.

Surface stabilizers useful herein physically adhere on the surface of the nanoparticulate active agent but do not chemically react with the active agent particles or itself. Individual molecules of the surface stabilizer are preferably essentially free of intermolecular cross-linkages.

Exemplary useful surface stabilizers include, but are not limited to, known organic and inorganic pharmaceutical excipients. Such excipients include various polymers, low molecular weight oligomers, natural products, and surfactants. Surface stabilizers include nonionic, ionic, anionic, cationic, and zwitterionic surfactants or compounds. Combinations of more than one surface stabilizer can be used in the invention.

Representative examples of surface stabilizers include hydroxypropyl methylcellulose, hydroxypropylcellulose, polyvinylpyrrolidone (PVP), random copolymers of vinyl pyrrolidone and vinyl acetate, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Dow); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2C(O)N(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$-dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl($C_{12-18}$) dimethylbenzyl ammonium chloride, N-alkyl($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™ (polyquanternium 10), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (quaternized ammonium salt polymers; Alkaril Chemical Company;), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;

(xi) two of $R_1$-$R_4$ are $CH_3$ and one of $R_1$-$R_4$ is a phenyl ring; or (xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

D. Particle Size of the Active Agent

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

For "nanoparticulate active agents," by "an effective average particle size of less than about 2 microns" it is meant that at 50%, by weight, of the active agent particles have a particle size of less than the effective average, e.g., less than about 2 microns, when measured by the above techniques. In other embodiments of the invention, at least about 70%, at least about 90%, at least about 95%, or at least about 99% of the active agent particles have a particle size of less than the effective average, i.e., less than about 2 microns.

In addition, in other embodiments of the invention, the effective average particle size of the nanoparticulate active agent particles can be less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm.

Preferably, following sterilization, the effective average particle size of the one or more nanoparticulate active agents is substantially the same as that prior to sterilization. In other embodiments of the invention, following sterilization, the effective average particle size of the one or more nanoparticulate active agents is preferably less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1 micron, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm.

Similarly, for "micronized active agents," "an effective average particle size of greater than about 2 microns" it is defined as at least about 50%, by weight, of the active agent particles have a particle size of greater than about 2 microns, when measured by the above techniques. In other embodiments of the invention, at least about 70%, at least about 90%, at least about 95%, or at least about 99% of the micronized active agent particles have a particle size of greater than about 2 microns.

E. Concentration of Nanoparticulate Active Agent and Surface Stabilizer

If the active agent is in a nanoparticulate particle size, then the active agent generally has one or more surface stabilizers associated with or adsorbed to the surface of the active agent. The relative amount of active agent and one or more surface stabilizers can vary widely. The optimal amount of the surface stabilizer(s) can depend, for example, upon the particular active agent selected, the equivalent hydrophilic lipophilic balance (HLB) of the active agent, the melting point, cloud point, and water solubility of the surface stabilizer, and the surface tension of water solutions of the stabilizer, etc.

The concentration of at least one active agent can vary from about 99.5% to about 0.001%, from about 95% to about 0.1%, or from about 90% to about 0.5%, by weight, based on the total combined weight of the at least one active agent and at least one surface stabilizer, not including other excipients.

The concentration of at least one surface stabilizer can vary from about 0.5% to about 99.999%, from about 5% to about 99.9%, and from about 10% to about 99.5%, by weight, based on the total combined dry weight of at least one active agent and at least one surface stabilizer, not including other excipients.

F. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrolidone, microcrystalline cellulose, such as Avicel® PH101 and Avicel® PH102, microcrystalline cellulose, and silicified microcrystalline cellulose (SMCC).

Suitable lubricants, including agents that act on the flowability of the powder to be compressed, are colloidal silicon dioxide, such as Aerosil® 200; talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, sodium chloride, Ringer's solution, lactated Ringer's solution, stabilizer solutions, tonicity enhancers (sucrose, dextrose, mannitol, etc.) polyols (propyleneglycol, polyethylene-glycol, glycerol, and the like), suitable mixtures thereof, vegetable oils (such as olive oil) and injectable organic esters such as ethyl oleate. Suitable fluids are referenced in Remington's Pharmaceutical Sciences, 17$^{th}$ edition, published by Mack Publishing Co., page 1543.

G. Methods of Making Nanoparticulate Active Agent Compositions

Dispersions of nanoparticulate active agents can be made using methods known in the art such as, for example, milling, homogenization, and precipitation techniques.

Exemplary methods of making nanoparticulate compositions are described in the '684 patent. In addition, methods of making nanoparticulate compositions are also described in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" U.S. Pat. No. 5,665,331, for "Co-Microprecipitation of Nanoparticulate Pharmaceutical Agents with Crystal Growth Modifiers;" U.S. Pat. No. 5,662,883, for "Co-Microprecipitation of Nanoparticulate Pharmaceutical Agents with Crystal Growth Modifiers;" U.S. Pat. No. 5,560,932, for "Microprecipitation of Nanoparticulate Pharmaceutical Agents;" U.S. Pat. No. 5,543,133, for "Process of Preparing X-Ray Contrast Compositions Containing Nanoparticles;" U.S. Pat. No. 5,534,270, for "Method of Preparing Stable Drug Nanoparticles;" U.S. Pat. No. 5,510,118, for "Process of Preparing Therapeutic Compositions Containing Nanoparticles;" and U.S. Pat. No. 5,470,583, for "Method of Preparing Nanoparticle Compositions Containing Charged Phospholipids to Reduce Aggregation," all of which are specifically incorporated by reference.

1. Milling to Obtain Dispersions of Nanoparticulate Active Agents

Milling of aqueous active agent dispersions to obtain a nanoparticulate dispersion comprises dispersing at least one active agent in a liquid dispersion media in which the active agent is poorly soluble. By "poorly soluble" it is meant that the active agent has a solubility in a liquid dispersion media of less than about 30 mg/ml, preferably less than about 10 mg/ml, and more preferably less than about 1 mg/ml. Such a liquid dispersion media can be, for example, water, aqueous salt solutions, oils such as safflower oil, and solvents such as ethanol, t-butanol, hexane, and glycol.

This is followed by applying mechanical means in the presence of grinding media to reduce the particle size of the active agent to the desired effective average particle size. The active agent particles can be reduced in size in the presence of at least one surface stabilizer. Alternatively, the active agent particles may be contacted with one or more surface stabilizers after attrition. Other compounds, such as a diluent, can be added to the active agent/surface stabilizer composition during the size reduction process. Dispersions can be manufactured continuously or in a batch mode.

2. Precipitation to Obtain Dispersions of Nanoparticulate Active Agents

Another method of forming the desired nanoparticulate composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the poorly water-soluble active agent in a suitable solvent; (2) adding the formulation from step (1) to a solution comprising at least one surface stabilizer to form a solution; and (3) precipitating the formulation from step (2) using an appropriate non-solvent. The method can be followed by removal of any formed salt, if present, by dialysis or diafiltration and concentration of the precipitate by conventional means. The precipitate can then be dispersed in a suitable dispersion media.

3. Homogenization to Obtain Dispersions of Nanoparticulate Active Agents

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing active agent particles in a liquid dispersion media, followed by subjecting the dispersion to homogenization to reduce the particle size of the active agent particles to the desired effective average particle size. The active agent particles can be reduced in size in the presence of at least one surface stabilizer. Alternatively, the active agent particles can be contacted with one or more surface stabilizers either before or after particle size reduction. It is preferred, however, to disperse the active agent particles in the liquid dispersion media in the presence of the at least one surface stabilizer as an aid to wetting of the active agent particles. Other compounds, such as a diluent, can be added to the active agent/surface stabilizer composition either before, during, or after the size reduction process. Dispersions can be manufactured continuously or in a batch mode.

H. Methods of Making Powders of Dispersions of Nanoparticulate Active Agents Powder forms of sterilized nanoparticulate active agent dispersions can be prepared by drying the nanoparticulate active agent dispersion following particle size reduction and sterilization. The powder can be formulated, for example, into a tablet, suppository, or other solid dosage form, the powder can be formulated into an aerosol for nasal or pulmonary administration, or the powder can be reconstituted into a liquid dosage form, such as ocular drops, liquid nasal and pulmonary aerosols, ear drops, injectable compositions, etc.

One benefit of the powders of sterile dispersions of nanoparticulate active agents according to the invention is that upon reconstitution in a liquid, the powders redisperse such that the effective average particle size of the redispersed active agent particles is less than about 2 microns. The redispersibility is observed with both solid dose and liquid dose formulations of nanoparticulate active agents. This is significant, because if upon administration, the nanoparticulate active agent particles present in the compositions of the invention did not redisperse to a substantially nanoparticulate particle size, then the dosage form may lose the benefits afforded by formulating the active agents into a nanoparticulate particle size.

This is because nanoparticulate active agent compositions benefit from the small particle size of the active agents; if the nanoparticulate active agent particles do not redisperse into the small particle sizes upon administration, then "clumps" or agglomerated active agent particles are formed. With the formation of such agglomerated particles, the bioavailability of the dosage form may fall.

Preferably, the redispersed active agent particles of the invention have an effective average particle size, by weight, which is substantially similar to that prior to sterilization. In other embodiments of the invention, the redispersed active agent particles of the invention have an effective average particle size, by weight, of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Moreover, the nanoparticulate active agent compositions of the invention—including liquid dispersions and solid dosage forms prepared from such dispersions—exhibit dramatic redispersion of the nanoparticulate active agent particles upon administration to a mammal, such as a human or animal, as demonstrated by reconstitution in a biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

1. Spray Drying of Nanoparticulate Active Agent Dispersions

A preferred drying method is spray drying. In an exemplary spray drying process, the nanoparticulate active agent dispersion is fed to an atomizer using a peristaltic pump and atomized into a fine spray of droplets. The spray is contacted with hot air in the drying chamber resulting in the evaporation of moisture from the droplets. The resulting spray is passed into a cyclone where the powder is separated and collected. The nanoparticulate dispersion can be spray-dried in the presence or absence of excipients to give the spray-dried intermediate powder.

2. Lyophilization

Solid dose or powder forms of sterilized dispersions of nanoparticulate active agents can also be prepared by lyophilizing the nanoparticulate active agent formulation following size reduction and sterilization.

In the lyophilization step, water is removed from the active agent nanoparticulate formulations after the dispersion is frozen and placed under vacuum, allowing the ice to change directly from solid to vapor without passing through a liquid phase. The lyophilization process consists of four interdependent processes, freezing, sublimation, the primary drying step, and desorption, which is the secondary drying step. Many lyophilizers can be used to achieve the lyophilization step of active agent nanoparticulate dispersions. Useful lyophilizers include those manufactured by FTS under the trademark DuraStop.

Suitable lyophilization conditions include, for example, those described in EP 0,636,365 (McNeil-PPC Inc.), U.S. Pat. No. 4,178,695 (A. Erbeia), and U.S. Pat. No. 5,384,124 (Farmalyoc), all of which are incorporated herein by reference. Typically, the nanoparticulate active agent dispersion is placed in a suitable vessel and frozen to a temperature of between about −5° C. to about −100° C. The frozen dispersion is then subjected to reduced pressure for a period of up to about 48 hours. The combination of parameters such as temperature, pressure, dispersion media, and batch size will impact the time required for the lyophilization process. Under conditions of reduced temperature and pressure, the frozen solvent is removed by sublimation yielding a solid, porous, immediate release solid dosage form having the active ingredient distributed throughout.

3. Granulation

Alternatively, a solid oral dosage form of the invention can be prepared by granulating in a fluidized bed an admixture comprising a sterilized nanoparticulate dispersion of active agent and at least one surface stabilizer with a solution of at least one pharmaceutically acceptable water-soluble or water-dispersible excipient, to form a granulate. This can be followed by tableting of the granulate to form a solid dosage form.

4. Tableting

The dosage formulations of the invention can be in the form of tablets. Preparation of such tablets can be by pharmaceutical compression or molding techniques known in the art. The tablets of the invention may take any appropriate shape, such as discoid, round, oval, oblong, cylindrical, triangular, hexagonal, and the like.

Powders for tableting can be formulated into tablets by any method known in the art. Suitable methods include, but are not limited to, milling, fluid bed granulation, dry granulation, direct compression, spheronization, spray congealing, and spray-dying. Detailed descriptions of tableting methods are provided in *Remington: The Science and Practice of Pharmacy*, 19th ed. Vol. 11 (1995) (Mack Publishing Co., Pennsylvania); and *Remington's Pharmaceutical Sciences*, Chapter 89, pp. 1633-1658 (Mach Publishing Company, 1990), both of which are specifically incorporated by reference.

The tablets may be coated or uncoated. If coated they may be sugar-coated (to cover objectionable tastes or odors and to protect against oxidation) or film coated (a thin film of water soluble matter for similar purposes).

I. Administration of the Compositions of the Invention

The present invention provides a method of treating a mammal, including a human, requiring administration of a sterile dosage form. The method comprises administering to a subject an effective amount of a sterile composition according to the invention.

The sterile compositions of the invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, sodium chloride, Ringer's solution, lactated Ringer's solution, stabilizer solutions, tonicity enhancers (sucrose, dextrose, mannitol, etc.) polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate active agent compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

One of ordinary skill will appreciate that effective amounts of an active agent can be determined empirically and can be employed in pure form or, where such forms exist, in pharmaceutically acceptable salt, ester, or prodrug form. Actual dosage levels of an active agent in the nanoparticulate compositions of the invention may be varied to obtain an amount of active agent that is effective to obtain a desired therapeutic response for a particular composition and method of administration. The selected dosage level therefore, depends upon the desired therapeutic effect, the route of administration, the potency of the administered active agent, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples have been set forth below for purposes of illustration and to describe the best mode of the invention at the present time. The scope of the invention is not to be in any way limited by the examples set forth herein.

Example 1

The purpose of the example was to prepare a γ-radiated aqueous dispersion of a nanoparticulate active agent (NanoCrystal® Colloidal Dispersion).

A dispersion of nanoparticulate naproxen, comprising 20% (w/w) naproxen and 2% (w/w) povidone K17 (BASF) as a surface stabilizer, was milled for 4.5 hrs under high energy milling conditions in a DYNO®-Mill KDL (Willy A. Bachofen A G, Maschinenfabrik, Basel, Switzerland) equipped with a 300 cc recirculation chamber and utilizing 500 μm polymeric attrition media.

The mean particle size (weight distribution) of the resultant naproxen dispersion was 117 nm, with 50% of the naproxen particles <93 nm, 90% of the naproxen particles <137 nm, and 95% of the naproxen particles <152 nm. Particle size analysis was performed with a Horiba LA-910 static light scattering particle size analyzer (Irvine, Calif.).

Portions of the dispersion were filled into glass vials which were then capped. The vials were subjected to varying doses of γ radiation (0, 15, 25, and 40 kGy). After approximately 20 months of storage at room temperature, the control sample (no radiation exposure) had a mean particle size of 298 nm, while the sample which received 25 kGy of radiation exposure had a mean particle size of 262 nm, with 50% of the naproxen particles <249 nm, 90% of the naproxen particles <380 nm, and 95% of the naproxen particles <430 nm.

The results show only a modest increase in particle size on storage at room temperature, and that exposure to γ-radiation did not adversely affect the particle size distribution of the sample.

Example 2

The purpose of the example was to describe the chemical analysis of the γ-radiated dispersions of nanoparticulate naproxen prepared in Example 1 after storage for 20 months at room temperature:

The radiated samples were analyzed by high pressure liquid chromatography (HPLC) according to the following approximate conditions:

Diluent: 70:30 (Acetonitrile:water)
Buffer Solution: 13.6 g Potassium Phosphate Monobasic in 2 L water. pH to 3.0 with Phosphoric acid. Add 20 mL of glacial acetic acid
Mobile Phase: 65:35 (buffer solution:acetonitrile)
Flow Rate: 1.3 mL/min
Run time: 25 minutes
Column temperature: 25° C.
Autosampler Temperature: ambient
Injection volume: 10 microliters
Detector wavelength: 270 nm
Column: Perkin-Elmer Brownlee™ Spheri-5, RP-8, 4.6 ID×250 mm, 5 μm particle size The HPLC system consisted of a quaternary pump with an autosampler, column oven, and variable ultraviolet spectrophotometric detector.

The standard concentration was 1 mg/mL diluted with diluent. Sample concentrations were also 1 mg/mL and prepared by diluting 250 mg of the nanoparticulate naproxen dispersion to 100 mL with diluent (or equivalent dilutions). Bracketing standards were used in the analysis with up to 5 samples between standards. Under these conditions, the parent peak attributable to naproxen had a retention time of approximately 18.7 minutes.

The only chemical impurity attributable to the γ radiation appeared at a retention time of approximately 25.8 minutes (relative retention time=1.38). This impurity was identified as 6-methoxyacetonaphthone, based on the retention time of an authentic sample of the same material (Sigma-Aldrich). Degradent concentrations are expressed on a % w/w basis relative to the naproxen concentration (for example, a degradent concentration of 1% would indicate that the mass of degradent present was $\frac{1}{100}^{th}$ the mass of naproxen present in the sample). The results summarized in Table 1 below show an impurity concentration dependence on the γ dose, and that very little chemical impurity was generated even at the highest radiation doses.

TABLE 1

| Impurity Content Following γ Radiation Exposure and Storage for 20 Months at Room Temperature | |
|---|---|
| Radiation Dose | Degradent Concentration (% w/w, rrt = 1.38) |
| 0 kGy | 0.0 |
| 15 kGy | 0.082 |
| 25 kGy | 0.13 |
| 40 kGy | 0.20 |

Example 3

The purpose of the example was to describe the manufacture and γ-radiation of a dispersion of a nanoparticulate active agent.

An aqueous dispersion of nanoparticulate naproxen having 36.4% (w/w) naproxen and 3.64% (w/w) povidone K17 PF, USP (BASF) as a surface stabilizer, adjusted to pH=7 with 2.7 g of 50% sodium hydroxide, was milled for 4.5 hrs in a DYNO®-Mill KDL (Willy A. Bachofen A G, Maschinenfabrik, Basel, Switzerland) equipped with a 300 cc recirculation chamber and utilizing 200 µm polymeric attrition media. The dispersion was then filtered through a 10 µm Whatman Poly-Cap® filter.

The mean particle size (weight distribution) of the milled naproxen dispersion was 85 nm, with 50% of the naproxen particles <82 nm, 90% of the naproxen particles <120 nm, and 95% of the naproxen particles <133 nm. Particle size analysis was performed with a Horiba LA-910 particle size analyzer (Irvine, Calif.).

The dispersion was dispensed into glass vials (approximately 2.5 g/vial) which were then capped. Some of the vials were subjected to 25 kGy of γ radiation; others were maintained as controls.

Particle size analysis was performed with a Horiba LA-910 particle size analyzer (Irvine, Calif.). Results of stability studies conducted at 5° C., 25° C. and 40° C. for 6 months are listed in Table 2 below. The particle size of the control samples stored at 25° C. and 40° C. demonstrated a slightly greater increase in particle size over the course of the study than the gamma irradiated samples. This data suggests gamma radiation is beneficial to the physical stability by creating a protective effect on the dispersions investigated here.

TABLE 2

Particle Size Following γ Radiation Exposure

| Sample | Timepoint | Storage Temperature, ° C. | Mean Particle Size (nm) |
|---|---|---|---|
| Control | initial | 25 | 128 |
|  | 1 month | 5 | 129 |
|  | 3 month | 5 | 130 |
|  | 6 month | 5 | 127 |
|  | 1 month | 25 | 143 |
|  | 3 month | 25 | 161 |
|  | 6 month | 25 | 168 |
|  | 1 month | 40 | 229 |
|  | 3 month | 40 | 203 |
|  | 6 month | 40 | 209 |
| γ-radiated | initial | 25 | 126 |
|  | 1 month | 5 | 127 |
|  | 3 month | 5 | 127 |
|  | 6 month | 5 | 122 |
|  | 1 month | 25 | 129 |
|  | 3 month | 25 | 129 |
|  | 6 month | 25 | 129 |
|  | 1 month | 40 | 144 |
|  | 3 month | 40 | 145 |
|  | 6 month | 40 | 146 |

Example 4

The purpose of the example was to describe the chemical analysis of the γ-radiated nanoparticulate naproxen samples prepared in Example 3.

The radiated samples of Example 3 were analyzed by high pressure liquid chromatography (HPLC) according to the approximate conditions described in Example 2. Under these conditions the retention time for the naproxen peak was 15.2 minutes.

The only chemical impurity attributable to the γ radiation appeared at a retention time of approximately 20.9 minutes (relative retention time=1.38). This impurity was identified as 6-methoxyacetonaphthone, based on the retention time of an authentic sample of the same material (Sigma-Aldrich). The results summarized in Table 3 below show the concentrations of the impurity as a function of time and storage temperature. In all cases, very little chemical impurity was generated.

TABLE 3

Impurity Content Following γ Radiation Exposure

| Sample | Timepoint | Storage Temperature, ° C. | Degradent Concentration (% w/w, rrt = 1.38) |
|---|---|---|---|
| Control | initial | 25 | 0.004 |
|  | 1 month | 5 | 0.000 |
|  | 3 month | 5 | 0.000 |
|  | 6 month | 5 | 0.000 |
|  | 1 month | 25 | 0.000 |
|  | 3 month | 25 | 0.000 |
|  | 6 month | 25 | 0.000 |
|  | 1 month | 40 | 0.000 |
|  | 3 month | 40 | 0.002 |
|  | 6 month | 40 | 0.003 |
| γ-radiated | initial | 25 | 0.019 |
|  | 1 month | 5 | 0.029 |
|  | 3 month | 5 | 0.032 |
|  | 6 month | 5 | 0.034 |
|  | 1 month | 25 | 0.037 |
|  | 3 month | 25 | 0.043 |
|  | 6 month | 25 | 0.044 |
|  | 1 month | 40 | 0.048 |
|  | 3 month | 40 | 0.056 |
|  | 6 month | 40 | 0.061 |

Example 5

The purpose of the example was to describe the manufacture and γ radiation of an aqueous dispersion of nanoparticulate naproxen:

A dispersion of nanoparticulate naproxen having 40% (w/w) naproxen and 4% (w/w) PVP K17 PF, as a surface stabilizer, pH adjusted to 6 to 7 with NaOH, was milled for 2.5 hrs under high energy milling conditions in a DYNO®-Mill KDL (Willy A. Bachofen A G, Maschinenfabrik, Basel, Switzerland) equipped with a 300 cc batch chamber and utilizing 200 µm polymeric attrition media.

The average particle size (weight distribution) of the milled nanoparticulate naproxen dispersion was 103 nm, with 50% of the naproxen particles <101 nm, 90% of the naproxen particles <131 nm, and 95% of the naproxen particles <143 nm. Particle size analysis was performed with a Horiba LA-910 particle size analyzer (Irvine, Calif.).

Post milling, 5% sucrose was added to the bulk material with moderate stirring. The bulk was filtered with a 5 µm filter. The bulk was filled into Type 1 glass vials (approximately 2.5 g/vial), stoppered and crimped. Vials were sent to a contract gamma irradiation facility where half were dosed with 25 kGray and half were not irradiated for use as controls.

Particle size analysis was performed with a Horiba LA-910 particle size analyzer (Irvine, Calif.). Effect of storage temperature and time on the particle size of the irradiated and control dispersion is illustrated in Table 4 below. As with Example 3, it appears gamma radiation may have a protective effect on the particle size of the formulations in this study, because the control samples had a slightly greater increase in particle size than the gamma irradiated samples.

TABLE 4

Particle Size Following γ Radiation Exposure

| Sample | Timepoint | Storage Temperature, °C. | Mean Particle Size (nm) |
|---|---|---|---|
| Control | initial | 25 | 121 |
| | 1 month | 5 | 121 |
| | 3 month | 5 | 125 |
| | 6 month | 5 | 121 |
| | 1 month | 25 | 144 |
| | 3 month | 25 | 157 |
| | 6 month | 25 | 163 |
| | 1 month | 40 | 236 |
| | 3 month | 40 | 193 |
| | 6 month | 40 | 192 |
| γ-radiated | initial | 25 | 118 |
| | 1 month | 5 | 119 |
| | 3 month | 5 | 120 |
| | 6 month | 5 | 113 |
| | 1 month | 25 | 124 |
| | 3 month | 25 | 129 |
| | 6 month | 25 | 126 |
| | 1 month | 40 | 160 |
| | 3 month | 40 | 171 |
| | 6 month | 40 | 165 |

Example 6

The purpose of this example was to describe the chemical analysis of the γ-radiated dispersions of nanoparticulate naproxen prepared in Example 5.

The radiated samples of Example 5 were analyzed by high pressure liquid chromatography (HPLC) according to the approximate conditions described in Example 2. The retention time of the naproxen peak was 15.2 minutes.

The only chemical impurity attributable to the γ radiation appeared at a retention time of approximately 20.9 minutes (relative retention time=1.38). This impurity was identified as 6-methoxyacetonaphthone, based on the retention time of an authentic sample of the same material (Sigma-Aldrich). The results summarized in Table 5 below show the concentrations of the impurity as a function of time and storage temperature. In all cases, very little chemical impurity was generated.

TABLE 5

Impurity Content Following γ Radiation Exposure

| Sample | Timepoint | Storage Temperature, °C. | Degradent Concentration (% w/w, rrt = 1.38) |
|---|---|---|---|
| Control | initial | 25 | 0.002 |
| | 1 month | 5 | 0.000 |
| | 3 month | 5 | 0.000 |
| | 6 month | 5 | 0.000 |
| | 1 month | 25 | 0.001 |
| | 3 month | 25 | 0.000 |
| | 6 month | 25 | 0.000 |
| | 1 month | 40 | 0.001 |
| | 3 month | 40 | 0.000 |
| | 6 month | 40 | 0.004 |
| γ-radiated | initial | 25 | 0.025 |
| | 1 month | 5 | 0.031 |
| | 3 month | 5 | 0.032 |
| | 6 month | 5 | 0.033 |
| | 1 month | 25 | 0.038 |
| | 3 month | 25 | 0.044 |
| | 6 month | 25 | 0.046 |
| | 1 month | 40 | 0.048 |
| | 3 month | 40 | 0.054 |
| | 6 month | 40 | 0.061 |

Example 7

The purpose of the example was to describe the manufacture and γ radiation of an aqueous dispersion of nanoparticulate budesonide:

An aqueous dispersion of nanoparticulate budesonide having 20% (w/w) budesonide and 2.2% (w/w) tyloxapol as a surface stabilizer, was milled for 6 hours in an Elan Magnetic Drive Mill (Nano Mill-1 system) recirculating through a 500 mL Gardner vessel with 200 μm polymeric attrition media. The dispersion was then diluted to 5% and filtered through a 0.8/0.2 μm Pall Supor capsule filter.

The mean particle size (weight distribution) of the milled budesonide dispersion was 84 nm, with 50% of the budesonide particles <83 nm, 90% of the budesonide particles <113 nm, and 95% of the budesonide particles <125 nm. Particle size analysis was performed with a Horiba LA-910 particle size analyzer (Irvine, Calif.).

The dispersion was diluted to 0.025% (w/w) budesonide in citrate/saline buffer, pH 4.7, and dispensed into glass vials (approximately 4.0 g/vial) which were then capped. Some of the vials were subjected to 25 kGy of γ radiation; others were maintained as controls.

Example 8

The purpose of the example was to report microbiological test results on the nanoparticulate budesonide prepared in Example 7.

Microbiological testing, including the Bacterial Endotoxin Test (BET) and sterility testing, were performed on the gamma irradiated budesonide samples. The results are set forth in Table 6 below.

TABLE 6

Bacterial Endotoxin Testing[1] Results by LAL Gel Clot Method Following γ Radiation Exposure

| Sample | Dilution | Specification | Result |
|---|---|---|---|
| 0.25 mg/mL budesonide | 1:2 | Report Results | <0.06 EU/mL (none detected) |

[1]Bacterial Endotoxin Testing - USP 27 <85>; ST3002SAM.7

The BET result of <0.06 EU/mL is also denoted as "none detected" in the analytical result, indicating the sample contains acceptable low levels of endotoxin.

Sterility analysis was conducted on post-gamma irradiated samples. The results are set forth in Table 7 below.

TABLE 7

Sterility Testing[1] Results Following γ Radiation Exposure

| Sample | Media | Specification | Result |
|---|---|---|---|
| 0.25 mg/mL budesonide | TSB[2] with Product | Report Results | No Growth |
| 0.25 mg/mL budesonide | FTM[3] with Product | Report Results | No Growth |

[1]Sterility Testing - USP 27, <71> p. 2157-2162 using Steritest
[2]TSB - Tryptic Soy Broth
[3]FTM - Fluid thioglycollate medium The data demonstrate that sterilization by gamma irradiation as stated in the present invention, produces a sterile product. This formulation met the sterility requirements set forth by USP 27 <71>.

The results obtained in the examples above illustrate that sterile injectable nanoparticulate formulations can be obtained by applying the method of the invention. Results obtained for particle size and assay, as well as the microbiological and sterility results, indicate that by using the method of the present invention, terminally sterilized nanoparticulate formulations are obtained which are suitable for parenteral administration.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A method for sterilization of a liquid dispersion of one or more nanoparticulate active agents by:
   (a) providing a liquid dispersion of at least one nanoparticulate active agent, wherein the dispersion comprises:
      an aqueous liquid dispersion media;
      (ii) at least one active agent which is poorly soluble in the liquid dispersion media and which has an effective average particle size of less than about 1 micron, and
      (iii) at least one surface stabilizer associated with the surface of the active agent; and
   (b) subjecting the dispersion to gamma irradiation;
   wherein said method produces a sterilized dispersion of one or more nanoparticulate active agents containing a degradant concentration of not more than 0.2% w/w of the active agent.

2. The method of claim 1, wherein the gamma irradiation is provided by applying cumulative doses of about 25 kGray.

3. The method of claim 1, wherein the gamma irradiation is provided by applying a dose selected from the group consisting of from about 5 to about 50 kGray, about 5 kGray to about 25 kGray, about 5 to about 20 kGray, about 5 to about 15 kGray, and about 5 to about 10 kGray.

4. The method of claim 1, wherein the dispersion is terminally sterilized.

5. The method of claim 1, wherein the sterilized dispersion of one or more nanoparticulate active agents is formulated for administration selected from the group consisting of oral, pulmonary, nasal, parenteral, rectal, local, buccal, and topical administration.

6. The method of claim 1, wherein prior to sterilization, the effective average particle size of the nanoparticulate active agent is selected from the group consisting of less than about 1 micron, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

7. The method of claim 1, wherein following sterilization, the effective average particle size of the one or more active agents is selected from the group consisting of less than about 1 micron, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

8. The method of claim 1, wherein the sterilization method results in a composition exhibiting increased particle size stability as compared to a control nanoparticulate active agent composition that has not been sterilized via gamma radiation.

9. The method of claim 1, wherein the active agent has a solubility in the liquid dispersion media selected from the group consisting of less than about 30 mg/ml, less than about 10 mg/ml, and less than about 1 mg/ml.

10. The method of claim 1, wherein the liquid dispersion media is selected from the group consisting of water and aqueous salt solutions.

11. The method of claim 1, wherein the concentration of at least one nanoparticulate active agent is selected from the group consisting of from about 99.5% to about 0.001%, from about 95% to about 0.1%, and from about 90% to about 0.5%, by weight, based on the total combined dry weight of the active agent and at least one surface stabilizer, not including other excipients.

12. The method of claim 1, wherein the concentration of at least one surface stabilizer is selected from the group consisting of from about 0.001 to about 99.5%, from about 0.1 to about 95%, and from about 0.5 to about 90%, by weight, based on the total combined dry weight of the active agent and at least one surface stabilizer, not including other excipients.

13. The method of claim 1, wherein at least one active agent is in a form selected from the group consisting of a crystalline phase, an amorphous phase, and a semi-crystalline phase.

14. The method of claim 1, wherein the active agent is selected from the group consisting of COX-2 inhibitors, retinoids, anticancer agents, NSAIDS, proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, anti epileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radio-pharmaceuticals, sex hormones, anti-allergic agents, stimulants, anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis, and respiratory illness therapies associated with acquired immune deficiency syndrome.

15. The method of claim 1, wherein the dispersion of one or more nanoparticulate active agents comprises at least two surface stabilizers.

16. The method of claim 1, wherein at least one surface stabilizer is selected from the group consisting of a nonionic surface stabilizer, an anionic surface stabilizer, a cationic surface stabilizer, an ionic surface stabilizer, and a zwitterionic surface stabilizer.

17. The method of claim 16, wherein at least one surface stabilizer is selected from the group consisting of cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone (PVP), 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, sodium lauryl sulfate, alkyl aryl polyether sulfonates, mixtures of sucrose stearate and sucrose distearate, triblock copolymers of the structure: —(—PEO—)—(—PBO—)—(—PEO—)—, p-isononylphenoxypoly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, random copolymers of vinyl acetate vinyl pyrrolidone, a cationic polymer, a cationic biopolymer, a cationic polysaccharide, a cationic cellulosic, a cationic alginate, a cationic nonpolymeric compound, a cationic phospholipids, cationic lipids, benzalkonium chloride, sulfonium compounds, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$-dimethyl hydroxyethyl ammonium chloride, $C_{12-15}$-dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl(ethenoxy)$_4$ ammonium chloride, lauryl dimethyl(ethenoxy)$_4$ ammonium bromide, N-alkyl($C_{12-18}$) dimethylbenzyl ammonium chloride, N-alkyl($C_{14-18}$)dimethylbenzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimethylaminoethyl methacrylate dimethyl sulfate, hexadecyltrimethyl ammonium bromide, poly(2-methacryloxyethyltrimethylammonium bromide) (S1001), poly(N-vinylpyrrolidone/2-dimethylaminoethyl methacrylate) di methylsulphate quarternary (S1002), and poly(2-methylacryloxyamidopropyltrimethylammonium chloride) (S1004).

18. The method of claim 1, further comprising lyophilizing, spray drying, or spray granulating the sterilized nanoparticulate active agent dispersion to form a powder.

19. The method of claim 18, wherein upon redispersion of the powder comprising one or more nanoparticulate active agents, the one or more nanoparticulate active agents have about the same particle size as that present prior to sterilization.

20. The method of claim 19, wherein redispersion is in a biorelevant media.

21. The method of claim 1 wherein the active agent is naproxen or budesonide.

22. A composition comprising a dispersion of one or more nanoparticulate active agents comprising:
 (a) an aqueous liquid dispersion media;
 (b) at least one active agent which is poorly soluble in the liquid dispersion media and which has an effective average particle size of less than about 1 micron, and
 (c) at least one surface stabilizer associated with the surface of the active agent;
 wherein the dispersion has been sterilized by subjecting the dispersion to gamma irradiation and
 wherein the dispersion contains a degradant concentration of not more than 0.2% w/w of the active agent.

23. The composition of claim 22, wherein the gamma irradiation is provided by applying a cumulative dose of about 25 kGray.

24. The composition of claim 22, wherein the gamma irradiation is provided by applying a dose selected from the group consisting of from about 5 to about 50 kGray, about 5 kGray to about 25 kGray, about 5 to about 20 kGray, about 5 to about 15 kGray, and about 5 to about 10 kGray.

25. The composition of claim 22, wherein the dispersion is terminally sterilized.

26. The composition of claim 22, wherein the sterilized dispersion of one or more nanoparticulate active agents is formulated for administration selected from the group consisting of oral, pulmonary, nasal, parenteral, rectal, local, buccal, and topical administration.

27. The composition of claim 22, wherein the effective average particle size of the nanoparticulate active agent, following sterilization via gamma radiation, is selected from the group consisting of less than about 1 micron, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

28. The composition of claim 22, wherein the sterilization method results in a composition exhibiting increased particle size stability as compared to a control nanoparticulate active agent composition that has not been sterilized via gamma radiation.

29. The composition of claim 22, wherein the active agent has a solubility in the aqueous liquid dispersion media selected from the group consisting of less than about 30 mg/ml, less than about 10 mg/ml, and less than about 1 mg/ml.

30. The composition of claim 22, wherein the aqueous liquid dispersion media is selected from the group consisting of water and aqueous salt solutions.

31. The composition of claim 22, wherein the concentration of at least one nanoparticulate active agent is selected from the group consisting of from about 99.5% to about 0.001%, from about 95% to about 0.1%, and from about 90% to about 0.5%, by weight, based on the total combined dry weight of the active agent and at least one surface stabilizer, not including other excipients.

32. The composition of claim 22, wherein the concentration of at least one surface stabilizer is selected from the group consisting of from about 0.001 to about 99.5%, from about 0.1 to about 95%, and from about 0.5 to about 90%, by weight, based on the total combined dry weight of the active agent and at least one surface stabilizer, not including other excipients.

33. The composition of claim 22, wherein at least one active agent is in a form selected from the group consisting of a crystalline phase, an amorphous phase, and a semi-crystalline phase.

34. The composition of claim 22, wherein the active agent is selected from the group consisting of COX-2 inhibitors, retinoids, anticancer agents, NSAIDS, proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radio-pharmaceuticals, sex hormones, anti-allergic agents, stimulants, anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organtransplant rejection therapies, therapies for tuberculosis, and respiratory illness therapies associated with acquired immune deficiency syndrome.

35. The composition of claim 22, wherein the dispersion of one or more nanoparticulate active agents comprises at least two surface stabilizers.

36. The composition of claim 22, wherein at least one surface stabilizer is selected from the group consisting of a nonionic surface stabilizer, an anionic surface stabilizer, a cationic surface stabilizer, an ionic surface stabilizer, and a zwitterionic surface stabilizer.

37. The composition of claim 36, wherein at least one surface stabilizer is selected from the group consisting of cetyl pyridinium chloride, gelatin, casein, phosphatides, dextran, glycerol, gum acacia, cholesterol, tragacanth, stearic acid, stearic acid esters and salts, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethyl cellulose, hydroxypropylmethyl-cellulose phthalate, noncrystalline cellulose, magnesium aluminum silicate, triethanolamine, polyvinyl alcohol, polyvinylpyrrolidone (PVP), 4-(1,1,3,3-tetramethylbutyl)-phenol polymer with ethylene oxide and formaldehyde, poloxamers, poloxamines, a charged phospholipid, dimyristoyl phophatidyl glycerol, dioctylsulfosuccinate, dialkylesters of sodium sulfosuccinic acid, sodium lauryl sulfate, alkyl aryl polyether sulfonates, mixtures of sucrose stearate and sucrose distearate, triblock copolymers of the structure: —(—PEO—)—(—PBO—)—(—PEO—)—, p-isononylphenoxypoly-(glycidol), decanoyl-N-methylglucamide; n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, a PEG derivatized phospholipid, PEG derivatized cholesterol, a PEG derivatized cholesterol derivative, PEG derivatized vitamin A, PEG derivatized vitamin E, random copolymers of vinyl acetate vinyl pyrrolidone, a cationic polymer, a cationic biopolymer, a cationic polysaccharide, a cationic cellulosic, a cationic alginate, a cationic nonpolymeric compound, a cationic phospholipids, cationic lipids, benzalkonium chloride, sulfonium compounds, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$ dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl(ethenoxy)$_4$ ammonium chloride, lauryl dimethyl(ethenoxy)$_4$ ammonium bromide, N-alkyl($C_{12-18}$) dimethylbenzyl ammonium chloride, N-alkyl($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, cationic guar, polymethylmethacrylate trimethylammonium bromide, polyvinylpyrrolidone-2-dimethylaminoethyl methacrylate dimethyl sulfate, hexadecyltrimethyl ammonium bromide, poly(2-methacryloxyethyltrimethylammonium bromide) (S1001), poly(N-vinylpyrrolidone/2-dimethylaminoethyl methacrylate) di methylsulphate quarternary (S1002), and poly(2-methacryloxyamidopropyltrimethylammonium chloride) (S1004).

38. The composition of claim 22, wherein the sterilized nanoparticulate active agent dispersion is lyophilized, spray dried, or spray granulated to form a powder.

39. The composition of claim 38, wherein upon redispersion of the powder comprising one or more nanoparticulate active agents, the one or more nanoparticulate active agents have about the same particle size as that present prior to sterilization.

40. The composition of claim 39, wherein redispersion is in a biorelevant media.

41. A dosage form comprising the composition of claim 22, wherein the dosage form is a solid, semi-solid, or liquid dosage formulation.

42. A dosage form comprising the composition of claim 22, wherein the dosage form is selected from the group consisting of controlled release formulations, solid dose fast melt formulations, aerosol formulations, lyophilized formulations, tablets, solid lozenge, capsules, powders, ocular formulations, formulations for administration to the ear, and liquids for injection.

43. A method of treating a mammal in need comprising administering a composition comprising a dispersion of one or more nanoparticulate active agents comprising:
    (a) an aqueous liquid dispersion media;
    (b) at least one active agent which is poorly soluble in the liquid dispersion media and which has an effective particle size of less than about 1 micron, and
    (c) at least one surface stabilizer associated with the surface of the active agent;
    wherein the dispersion has been sterilized by subjecting the dispersion to gamma irradiation and
    wherein the dispersion contains a degradant concentration of not more than 0.2% w/w of the active agent.

* * * * *

UNITED STATES PATENT AND TRADEMARK OFFICE
CERTIFICATE OF CORRECTION

| | | |
|---|---|---|
| PATENT NO. | : 7,842,232 B2 | Page 1 of 1 |
| APPLICATION NO. | : 10/851661 | |
| DATED | : November 30, 2010 | |
| INVENTOR(S) | : Bosch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this
Fifteenth Day of March, 2011

David J. Kappos
*Director of the United States Patent and Trademark Office*